United States Patent
Helmer et al.

(10) Patent No.: US 11,857,708 B2
(45) Date of Patent: Jan. 2, 2024

(54) DEVICE FOR ATTACHMENT TO AN INJECTION DEVICE

(71) Applicant: SANOFI, Paris (FR)

(72) Inventors: Michael Helmer, Frankfurt am Main (DE); Christian Rehbein, Nieder-Olm (DE)

(73) Assignee: Sanofi, Paris (FR)

(*) Notice: Subject to any disclaimer, the term of this patent is extended or adjusted under 35 U.S.C. 154(b) by 637 days.

(21) Appl. No.: 16/956,370

(22) PCT Filed: Dec. 17, 2018

(86) PCT No.: PCT/EP2018/085116
§ 371 (c)(1),
(2) Date: Jun. 19, 2020

(87) PCT Pub. No.: WO2019/121452
PCT Pub. Date: Jun. 27, 2019

(65) Prior Publication Data
US 2021/0106761 A1   Apr. 15, 2021

(30) Foreign Application Priority Data

Dec. 20, 2017 (EP) .................................. 17306845

(51) Int. Cl.
*A61M 5/315* (2006.01)
*A61M 5/20* (2006.01)
*A61M 5/31* (2006.01)

(52) U.S. Cl.
CPC ........ *A61M 5/3155* (2013.01); *A61M 5/2033* (2013.01); *A61M 2005/3126* (2013.01);
(Continued)

(58) Field of Classification Search
CPC .... A61M 5/3155; A61M 5/2033; A61M 5/20; A61M 5/24; A61M 2005/3126;
(Continued)

(56) References Cited

U.S. PATENT DOCUMENTS

| | | | |
|---|---|---|---|
| 6,277,099 B1 | 8/2001 | Strowe et al. | |
| 2006/0153693 A1* | 7/2006 | Fiechter | A61M 5/31555 417/63 |

(Continued)

FOREIGN PATENT DOCUMENTS

| | | |
|---|---|---|
| CN | 103957961 | 7/2014 |
| CN | 104220116 | 12/2014 |

(Continued)

OTHER PUBLICATIONS

PCT International Preliminary Report on Patentability in International Appln. No. PCT/EP2018/085116, dated Jun. 23, 2020, 8 pages.

(Continued)

*Primary Examiner* — Theodore J Stigell
*Assistant Examiner* — Nidah Hussain
(74) *Attorney, Agent, or Firm* — Fish & Richardson P.C.

(57) ABSTRACT

A supplementary device configured to be attached to a drug delivery device, the supplementary device including: first means being adapted to mechanically couple the supplementary device to a dosage selector of the drug delivery device; second means being adapted to select a dosage to be delivered by the drug delivery device; third means being adapted to mechanically couple the second means to the first means such that a dosage selection made with the second means generates a torque being transferred via the third means to the first means; a sensor configured to output signals indicative of the generated torque; and electronics (Continued)

configured to receive the signals output from the sensor and to determine based on the signals the selected dosage.

22 Claims, 11 Drawing Sheets

(52) U.S. Cl.
CPC ............... *A61M 2205/332* (2013.01); *A61M 2205/3327* (2013.01); *A61M 2205/3584* (2013.01); *A61M 2205/52* (2013.01); *A61M 2205/8206* (2013.01)

(58) Field of Classification Search
CPC .... A61M 2205/332; A61M 2005/3327; A61M 2205/3584; A61M 2205/52; A61M 2205/8206; A61M 2005/3142; A61M 2005/2006; A61M 5/31565; A61M 5/31533; A61M 2205/3215; A61M 2005/3139; G16H 20/17
USPC ........................................................ 604/207
See application file for complete search history.

(56) References Cited

U.S. PATENT DOCUMENTS

| | | | |
|---|---|---|---|
| 2008/0161796 A1* | 7/2008 | Cao ................. | A61B 18/1492 606/41 |
| 2013/0204224 A1 | 8/2013 | Mueller-Pathle et al. | |
| 2014/0074041 A1* | 3/2014 | Pedersen ........... | A61M 5/31541 604/211 |
| 2014/0243750 A1 | 8/2014 | Larsen et al. | |
| 2014/0276583 A1* | 9/2014 | Chen ................. | A61M 5/31546 604/207 |
| 2016/0206823 A1* | 7/2016 | Jugl .................... | A61M 5/3146 |
| 2018/0154086 A1* | 6/2018 | Toporek ............ | A61M 5/31528 |

FOREIGN PATENT DOCUMENTS

| | | | |
|---|---|---|---|
| CN | 104981262 | 10/2015 | |
| CN | 105073165 | 11/2015 | |
| CN | 106999655 | 8/2017 | |
| JP | H11-56922 | 3/1999 | |
| JP | 2012-519025 | 8/2012 | |
| JP | 2013-521909 | 6/2013 | |
| JP | 2014-531283 | 11/2014 | |
| WO | WO 2010/098927 | 9/2010 | |
| WO | WO 2011/053832 | 5/2011 | |
| WO | WO 2011/113806 | 9/2011 | |
| WO | WO 2012/046199 | 4/2012 | |
| WO | WO 2013/050535 | 4/2013 | |
| WO | WO 2013/120777 | 8/2013 | |
| WO | WO 2014/037331 | 3/2014 | |
| WO | WO 2014/128156 | 8/2014 | |
| WO | WO 2014/128157 | 8/2014 | |
| WO | WO 2016/091840 | 6/2016 | |
| WO | WO 2016/198516 | 12/2016 | |
| WO | WO 2017/102742 | 6/2017 | |
| WO | WO 2017/165207 | 9/2017 | |
| WO | WO 2017/186955 | 11/2017 | |
| WO | WO-2019121448 A1 * | 6/2019 | ............. A61M 5/24 |

OTHER PUBLICATIONS

PCT International Search Report and Written Opinion in International Appln. No. PCT/EP2018/085116, dated Feb. 28, 2019, 10 pages.

* cited by examiner

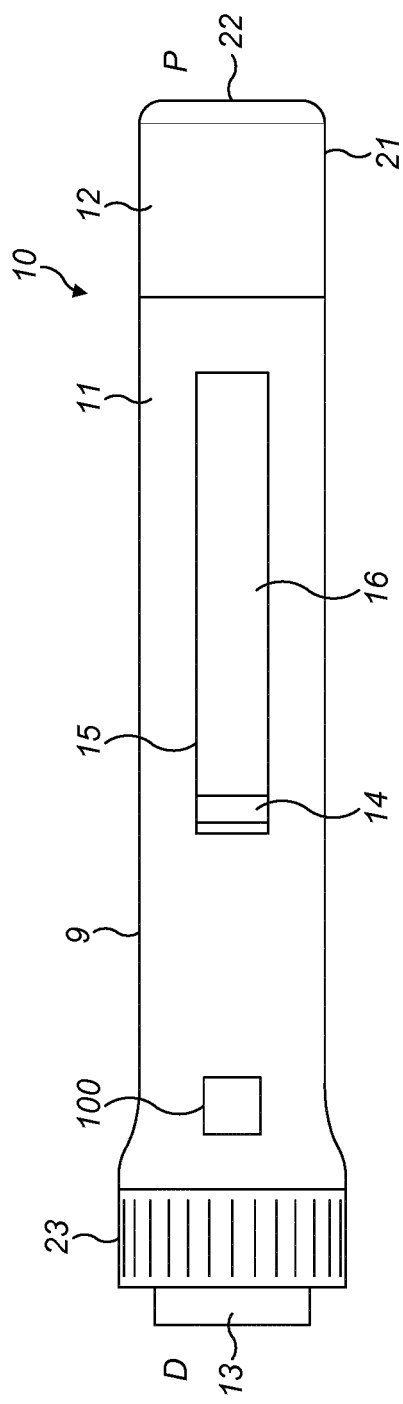
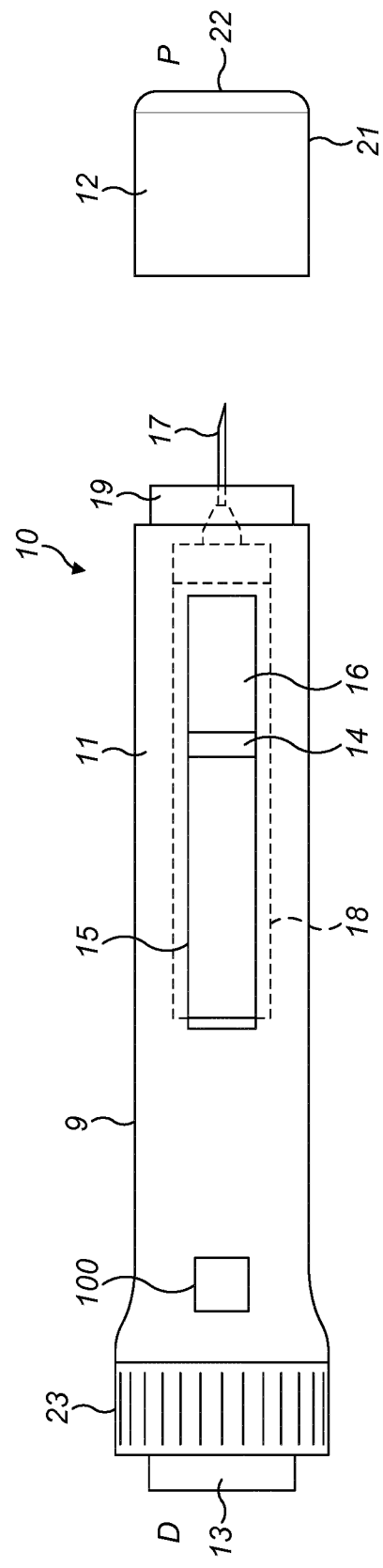
FIG. 1A
FIG. 1B

DEVICE FOR ATTACHMENT TO AN INJECTION DEVICE

CROSS REFERENCE TO RELATED APPLICATIONS

The present application is the national stage entry of International Patent Application No. PCT/EP2018/085116, filed on Dec. 17, 2018, and claims priority to Application No. EP 17306845.3, filed on Dec. 20, 2017, the disclosures of which are herein incorporated by reference.

TECHNICAL FIELD

The present disclosure relates to a device configured to retain an injection device or syringe and being able to detect a selected dosage for injection.

BACKGROUND

A variety of diseases exist that require regular treatment by injection of a medicament. Such injection can be performed by using injection devices, which are applied either by medical personnel or by patients themselves.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages for the user from this approach. If the user stops pressing the button/plunger, then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, allergies, hormone therapies, anticoagulants etc. Auto-injector devices can be used to deliver a single dose of a particular life-saving drug. For example they are often prescribed to people who are at risk for anaphylaxis. They are also often used in the military to protect personnel from chemical warfare agents. Alternatively, auto-injectors are used to administer medicaments according to a prescribed therapeutic schedule for people suffering from Multiple Sclerosis, Rheumatroid Arthritis, Anemia, etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Forces required of the user/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

Auto-injectors may be disposable or single use devices which may only be used to deliver one dose of medicament and which have to be disposed of after use. Other types of auto-injectors may be reusable. Usually they are arranged to allow a user to load and unload a standard syringe. The reusable auto-injector may be used to perform multiple parenteral drug deliveries, whereas the syringe is disposed after having been spent and unloaded from the auto-injector. The syringe may be packaged with additional parts to provide additional functionality.

In a typical scenario a disease can be treated by patients themselves by injection of medicament doses using an auto-injector, for example on a daily, weekly, bi-weekly, or monthly basis.

The correct administration of drugs and its termination is important for the safety and efficacy of the drug (pharmacovigilance). Failures in administration through the user can be minimized by monitoring of the injection device and the application time. Typical patient failures are:

1. The user may forget the correct day of maturity for their next injection. This is particularly the case for medication intervals longer than a day, e.g., twice a week, every second day, bi-weekly, or therapy specific intervals such as $1^{st}$ week twice, $2^{nd}$ week every $2^{nd}$ day, as of third week 2, 2, 3—interval.
2. The user may let too much time pass between removing the auto injector cap and performing the injection, resulting in needle clogging and/or device stalling.
3. The user does not carry out the holding time (also know as "dwell time") after the end of injection.

SUMMARY

This disclosure describes a re-usable add-on device suitable for use with one shot auto-injectors and which may record the injection history, monitor the dose administration and aid the patient in performing the injection correctly and on time.

A first aspect provides a supplementary device configured to be attached to a drug delivery device, the supplementary device comprising:
   first means being adapted to mechanically couple the supplementary device to a dosage selector of the drug delivery device;
   second means being adapted to select a dosage to be delivered by the drug delivery device;
   third means being adapted to mechanically couple the second means to the first means such that a dosage selection made with the second means generates a torque being transferred via the third means to the first means;
   a sensor configured to output signals indicative of the generated torque; and
   electronics configured to receive the signals output from the sensor and to determine based on the signals the selected dosage.

The electronic determination of the selected dosage has the advantage of being further processed for example by an external electronic device such as a smartphone or computer, particularly a mobile computer like a tablet PC or a laptop PC, or an electronic medicament injection assistant device. Further processing may for example comprise displaying the selected dosage on the external device for information, or comparing the determined selected dosage with a prescribed dosage and informing a user of a deviation of the selected dosage from the prescribed dosage. Also, the determined selected dosage may be stored for later processing or evaluation. The supplementary device may be implemented with less components reducing technical complexity and, thus, production costs. Another advantage is reusability, which means that the supplementary device can be designed such that be used with several drug delivery devices. The first means can be designed such that it may be even used with different drug delivery devices. For example, it may be provided that the first means may adaptable to the kind of drug delivery device with which the supplementary device should be used. The drug delivery devices can be designed for dosage selection and can have a dosage selector, to which the first means may be mechanically coupled.

The second means may be further adapted to trigger a release button of the drug delivery device for injection of the selected dosage and the third means may be further adapted to transfer a compressive force exerted on the second means for injection to the release button. For example, the second means may comprise a button for activating the release button of the drug delivery device. When a user presses this button, it triggers the release button of the drug delivery device since the compression force exerted by the user on the button is transferred by the third means to the release button.

The supplementary device may further comprise a spring forcing the second means into an initial position, in which no compressive force is exerted on the release button of the drug delivery device. The forcing of the second means into the initial position may be for example processed by the electronics for detecting the end of an injection.

In an implementation, the third means may comprise at least one spring for torque transmission. One end of the at least one spring may be fixedly coupled to the second means and the other end may be arranged to exert a force on the sensor upon generation of a torque via the second means. The electronics may be configured to receive as the signals output from the sensor a force measurement and to determine based on the force measurement the selected dosage.

In another implementation, the third means may comprise one spring for torque transmission, and both ends of the spring may be fixedly coupled to the second means and the spring may be shaped to exert a force on the sensor upon generation of a torque via the second means. The electronics may be configured to receive as the signals output from the sensor a force measurement and to determine based on the force measurement the selected dosage.

In yet another implementation, the third means may comprise the sensor, and the sensor may comprise at least one element made of a quantum tunnelling composite material. A change of the torque being generated upon the dosage selection may then result in a resistance change of the at least one element made of a quantum tunnelling composite material. The electronics may be configured to receive as the signals output from the sensor the resistance change and to determine based on the received resistance change the selected dosage.

In still another implementation, the third means may comprise a coupling plate, a sensor wheel and a pin being fixedly coupled to the second means and extending through a bearing in the wheel to a release button of the drug delivery device such that exertion of a pressure force on the second means is transferred by the pin to the release button. The bearing may comprise an anti-rotation lock such that a rotation of the pin is transferred to the wheel. The wheel may be further coupled to the coupling plate such that a rotation of the second means is transferred to the wheel. The wheel may be coupled to the coupling plate such that a rotation of the wheel is restricted and the wheel may comprise at least two bendable spokes with at least one of the spokes comprising a sensor element being adapted to measure a bending of the at least one spoke. The electronics may be configured to receive as the signals output from the one or more sensor elements the measured bending(s) and to determine based on the received bending(s) measurements the selected dosage. The sensor element may be made from one of the following sensor materials in combination with a wheel material: a quantum tunnelling composite material combined with a rubber wheel; a force sensing resistor material combined with a plastic wheel; a strain gauge sensor material combined with a plastic or metal wheel.

The electronics of the supplementary device may be configured to process the received signals output from the sensor by performing peak measurements of the signals output indicative of an operation of the second means and by counting measured peaks for determining the selected dosage. Peaks may be particularly generated during a dosage selection, for example when a user dials a desired dosage. The electronics may then "count the clicks" through the peak measurements and derive from the counted peaks the selected dosage.

The second means may comprise a printed circuit board with the electronics and a battery for supplying the electronics of the printed circuit board and the sensor. The printed circuit board and the battery may be for example shaped such that both can be arranged as batch within the second means, which can be designed as a knob or cap covering the printed circuit board, the battery, the third means and at least partly the first means.

The electronics may comprise a communication circuitry configured to communicate with an external electronic device. The communication circuitry may for example comprise a wireless unit for transmitting data to and/or receive data from one or more external devices.

The electronics may be configured to transmit the determined selected dosage and/or to receive data via the communication circuitry. For example, the determined selected dosage could be transmitted to the user's computer or smart phone wirelessly, for example over a Bluetooth® connection.

The supplementary device may be adapted to detect a mechanically coupling to a dosage selector of the drug delivery device and to supply the electronics with electrical energy upon the detection. For example, the first means may comprise a switch, which may be activated when the first means are coupled to a dosage selector of a drug delivery device, particularly when the first means are clipped on the dosage selector. The activation of the switch may then connected the battery and the electronics so that the electronics is powered on and may operate.

The supplementary device may further comprise a display unit, for example a LCD (Liquid Crystal Display) or an electronic ink display. The electronics may be configured to control the display unit such that a selected dosage is displayed on the display unit.

The electronics may comprise a processor and at least one memory, and the processor may be configured to cause information relating to a selected dosage and/or a last performed injection operation to be stored in the memory upon determining that an injection was made with the drug delivery device. The information may comprise at least a time stamp associated with the last performed injection operation.

A second aspect provides a system comprising the supplementary device of the first aspect and the drug delivery device. The drug delivery device may be a powered auto-injector. A dispensing mechanism of the powered auto-injector may be powered by a pre-compressed spring.

BRIEF DESCRIPTION OF THE FIGURES

The figures show:

FIG. 1: an exploded view of an injection device;

DETAILED DESCRIPTION

Figure 2:
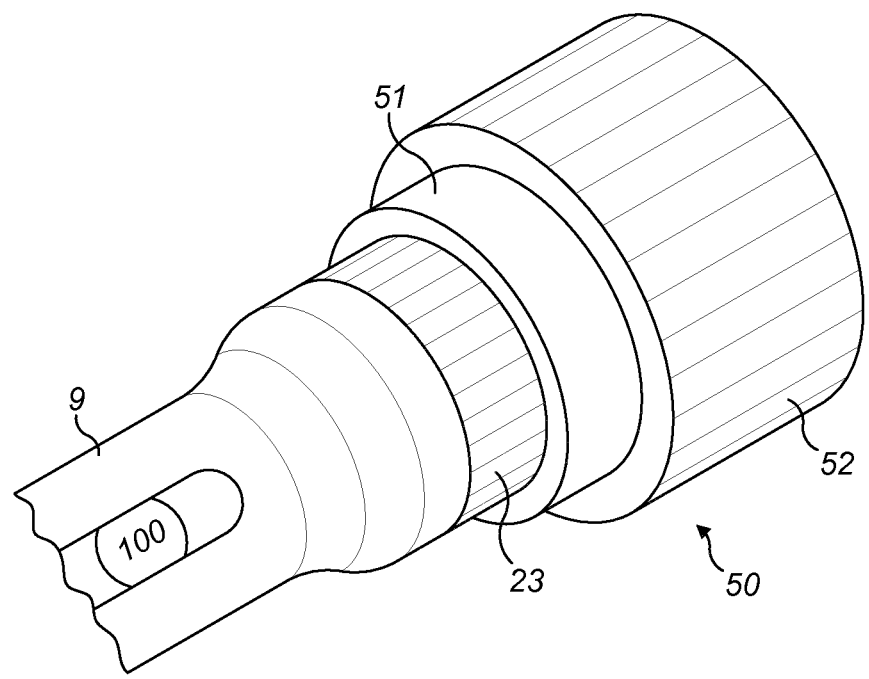
FIG. 2: a perspective illustration of a first embodiment of a supplementary device for releasably attachment to the injection device of FIG. 1 according to an aspect of the present disclosure.

In the following, embodiments of the present disclosure will be described with reference to an auto-injector. The present disclosure is however not limited to such application and may equally well be deployed with injection devices that eject other medicaments, or with other types of drug delivery devices, such as syringes, pre-filled syringes, needleless injectors and inhalers.

An injection device 10 according to embodiments will now be described with reference to FIGS. 1A and 1B. In some embodiments, the injection device 10 is a single use auto-injector 10. The auto-injector 10 has a proximal end P and a distal end D. The proximal end P is directed towards the injection site of a patient during an injection while the distal end D is directed away from the injection site.

The auto-injector 10 comprises a body 9 and a cap 12 (also referred to herein as the outer needle cap or ONC 12). The body 9 comprises an outer housing 11. The outer housing 11 is an elongate tube. The outer housing 11 includes a cartridge holder or syringe holder (not shown) which supports a cartridge or syringe 18 containing liquid medicament 16. Hereafter the description shall refer to a cartridge 18, which is supported by a cartridge holder (not shown). The cartridge 18 is shown in broken lines in FIG. 1B.

The outer housing 11 also houses a dispense mechanism (not shown) for causing dispensing of the medicament 16 during injection.

A hollow needle 17 communicates with an interior volume of the cartridge 18 and serves as a conduit for liquid medicament 16 during injection. The needle 17 and the cartridge 18 are in a fixed position relative to each other and to the body 9. A stopper, plunger, piston or bung 14 is moveable within the cartridge 18 to as to expel medicament contained within the cartridge 18 through the needle 17 under action of the dispense mechanism.

The dispense mechanism is mechanically coupled to the piston 14 of cartridge 18. The dispense mechanism is configured to move the piston axially along the cartridge 18 in a proximal direction to dispense medicament 16 through the needle 17. The dispense mechanism includes components that cooperate to apply a force to the piston 14 in response to an actuation input provided by a user. Here, the actuation input that triggers application of a force to the piston 14 is received by way of a dose dispense button 13 that is located at the distal end of the auto-injector 10. The dispense mechanism is mechanically coupled to the dispense button 13.

The body 9 further comprises a dosage selector 23 at the distal end of the outer housing 11. The dosage selector 23 allows to manually select a dosage to be injected by rotating it clockwise. An internal mechanism (not shown) is mechanically coupled to the dispense mechanism in order to adjust it for injection of a selected dosage.

The body 9 also comprises a cap support 19 at the proximal end of the outer housing 11. The cap support is concentric with the outer housing 11 and may have a smaller diameter. The cap support 19 extends from the proximal end of the housing 11. The ONC 12 is received over the cap support 19 to close the proximal end of the body 9 and to cover the needle 17. The ONC 12 comprises a cylindrical wall 21 and an end wall 22. With the ONC 12 located on the body 9, as shown in FIG. 1A, an internal surface of the cylindrical wall 21 abuts an external surface of the cap support 19 in tightly abutting relation so that the ONC 12 is retained thereon in an attached position.

Before injecting the medicament 16, the user select via the dosage selector 23 the dose to be injected. To inject the medicament 16, the ONC 12 is removed from the device 10 by the user, resulting in the arrangement shown in FIG. 1B. Next, the proximal end of the auto-injector 10 is placed against an injection site of a patient, which may be the user or another person. The user then actuates the dispense button 13. This causes the dispense mechanism to force the piston 14 to expel medicament from the cartridge 18 through the needle 17 into the injection site of the patient.

The cartridge 18 is transparent and a window 15 is provided in the housing 11 coincident with the cartridge 18 so that the medicament 16 contained within the cartridge 18 is visible. A user of the auto-injector this is able by inspection to determine whether the entire quantity of medicament 16 has been ejected from the cartridge 18 during the injection.

A label is provided on the housing 11. The label includes information 100 about the medicament included within the injection device 10, including information identifying the medicament. The information 100 identifying the medicament may be in the form of text. The information 100 identifying the medicament may also be in the form of a color. The information 100 identifying the medicament may also be encoded into a barcode, QR code or the like. The information 100 identifying the medicament may also be in the form of a black and white pattern, a color pattern or shading.

FIG. 2 is a schematic illustration of an embodiment of a supplementary device 50 to be releasably attached to injection device 10 of FIG. 1. Supplementary device 50 comprises a carrier interface 51 configured to mechanically couple to the dosage selector 23 of injection device 10 of FIG. 1, particularly to be clamped on the dosage selector 23 so that a rotation of the interface 51 is transferred to the dosage selector 23. Supplementary device 50 further comprises a dial knob 52 for dosage selection. Dial knob 52 overlaps carrier interface 51 at least partly.

Figure 3:
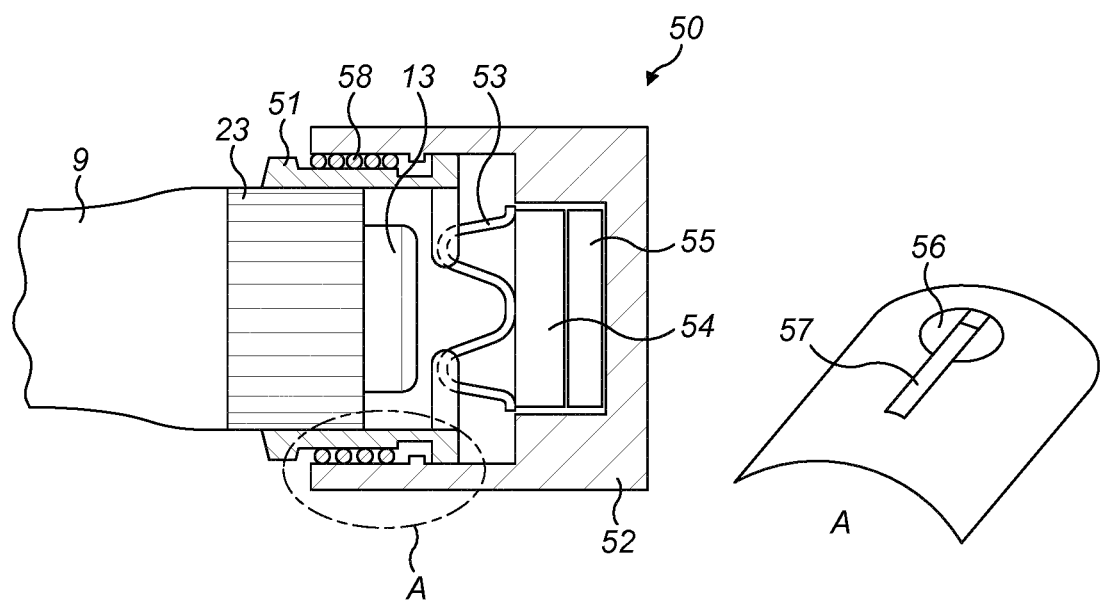
FIG. 3: a cutaway illustration of the first embodiment.

FIG. 3 is a cutaway illustration of the first embodiment of the supplementary device 50 showing the inner mechanism for dosage selection. The carrier interface 51 is clamped on the dosage selector 23 of the injection device. A metal spring 53 is mounted on a printed circuit board (PCB) 54, which comprises electronics and a sensor, for torque transmission and definition of a resetting position of the dial knob 52. A battery 55 for supplying the electronics of the PCB 54 is arranged between the PCB 54 and the inner side of the dial knob 52. Two guidance 56, 57 are comprised in/on the outer side of the carrier interface 51, as can be seen in the view A. The guidance 56, 57 are provided for the dial knob 52, which serves two functions, namely dosage selection by turning it around the axis of the body 9 and injection by pressing it down to the release button 13 of the injection device. The guidance 57 prevents a damage of the sensor and/or the spring 53 when the device end stop is reached, and defines the resetting position of the dial knob 52. The guidance 56 prevents an overwinding of the dial knob 52. A further spring 58 is arranged between the carrier interface 51 and the dial knob 52 such that it pushes the dial knob 52 in the resetting position.

Figure 4:
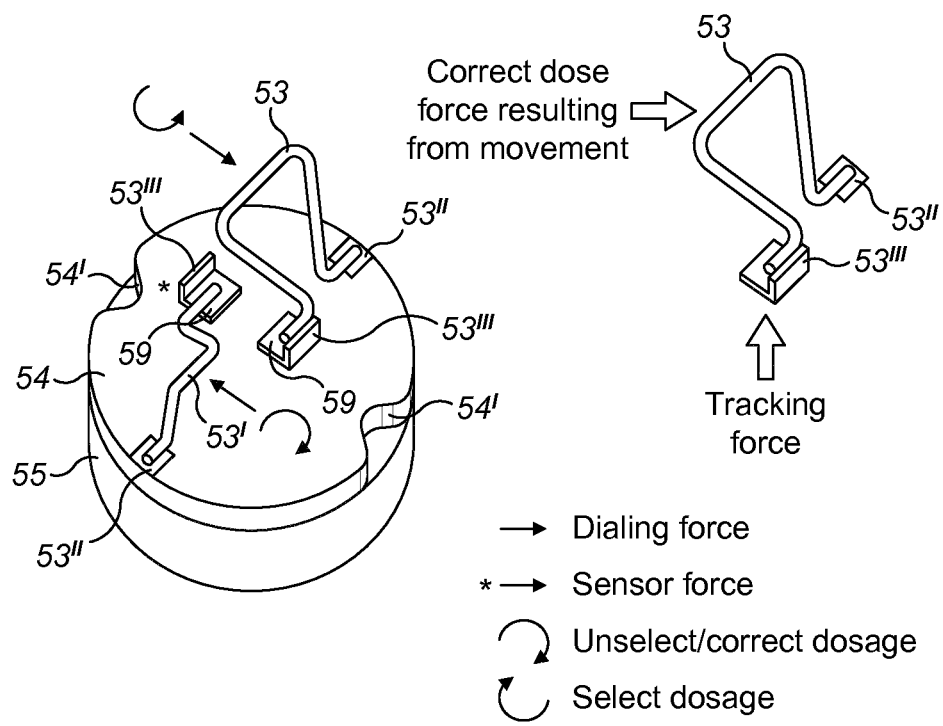
FIG. 4: perspective illustrations of an implementation with two springs and their arrangement on a printed circuit board of the first embodiment.
Figure 5:
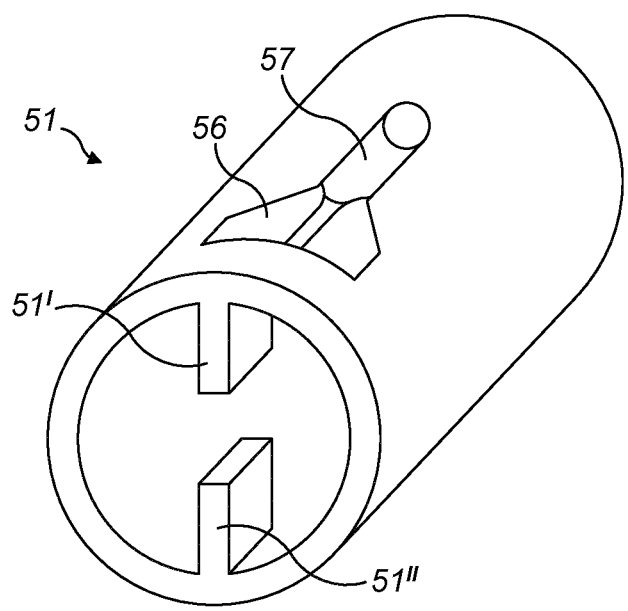
FIG. 5: perspective illustrations of the carrier interface to an injection device of the first embodiment.

FIG. 4 shows perspective illustrations of an implementation with two springs 53, 53' and their arrangement on the PCB 54. Both springs 53, 53' are welded on one end 53" to the PCB 54. The other ends of the springs 53, 53' are freely movable arranged over sensor elements 59 on the PCB 54. End stops 53''' restrict the movement of the freely movable spring ends in a respective direction. When a user turns the dial knob 52 to select a dosage (clockwise) or to unselect or correct a selected dosage (counter-clockwise), a dialing force is exerted on the springs 53, 53' via cams 51', 51'' (FIG. 5) provided within the dial knob 52, which results in a movement of the freely movable spring ends over the sensor elements 59. A rotation of the PCB 54 is prevented by anti-rotation locks 54'. The movements of the spring ends are restricted by the end stops 53''' arranged at the sensor elements 59. Movements of the spring ends over the sensor elements 59 may cause sensor signals, which may be detected by an electronics of the PCB 54 and processed to determine a selected dosage, as will be explained with reference to FIG. 16 later.

Figure 6:
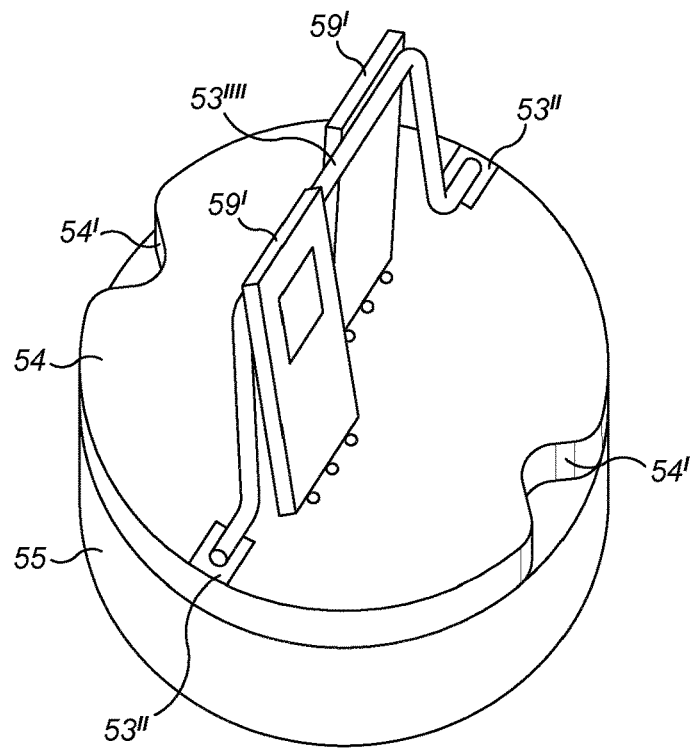
FIG. 6: a perspective illustration of an implementation with one spring and its arrangement on a printed circuit board of the first embodiment.

FIG. 6 is a perspective illustration of another implementation with one spring 53'''' and its arrangement on the PCB 54. The two ends of the spring 53'''' are both welded near opposing edges of the PCB 54. The spring 53'''' contacts two sensor elements 59', which are welded on one of their sides on the PCB 54. One sensor element is provided for detecting a left-hand turn of the dial knob 52 (for example, when unselecting a dose), and the other sensor is provided for detecting a right-hand turn of the dial knob 52 (for example, when selecting a dose). Both sensor elements 59' are arranged on different sides of the spring 53''''.

Figure 7:
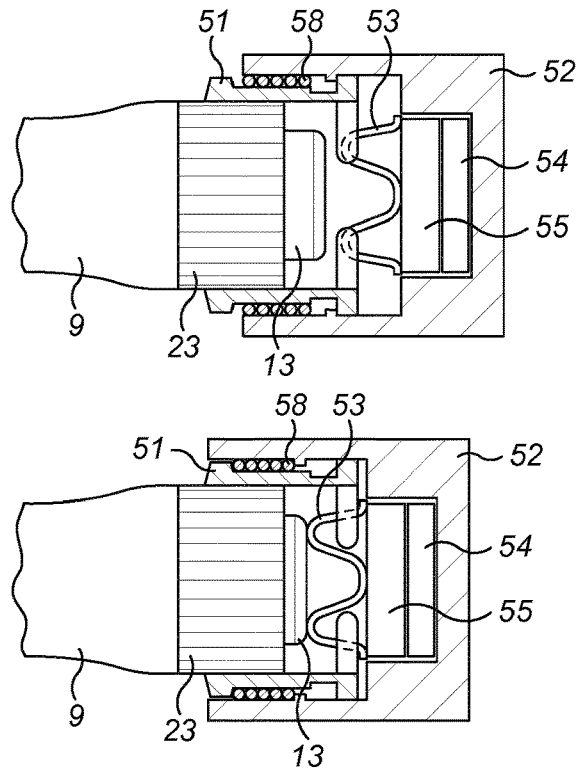
FIG. 7: two cutaway illustrations of the first embodiment with the dosage selection knob in two different statuses.

FIG. 7 shows two cutaway illustrations of the first embodiment with the dosage selection or dial knob 52 in two different statuses. The above illustration shows the status of unused or dialing or selecting a dosage with no pressure exerted on the dial knob 52. The below illustration shows the status of an injection, when the dial knob 52 is pushed down.

Figure 16:
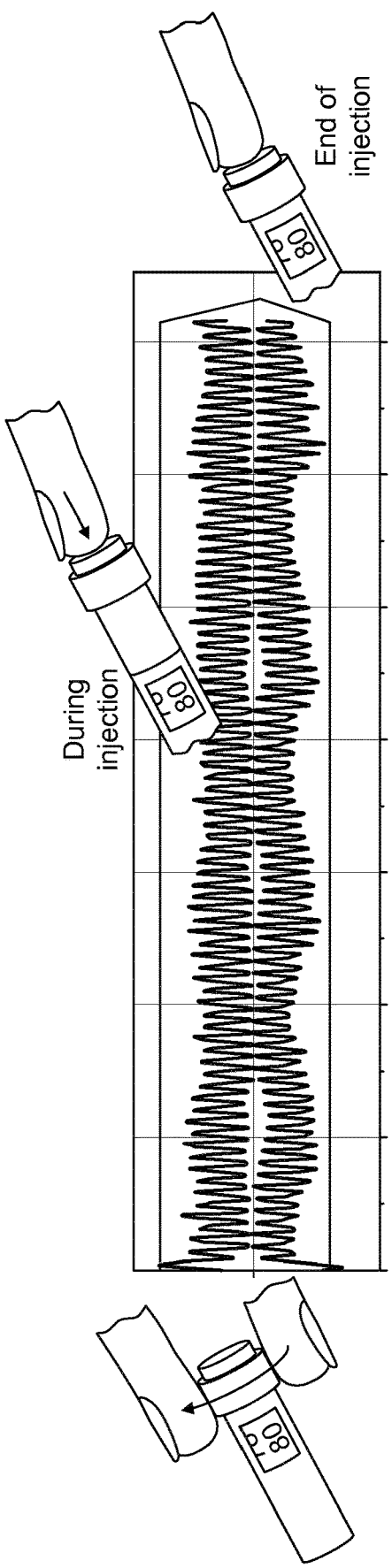
FIG. 16: a diagram of an example course of a signal generated by a sensor according to an aspect of the present disclosure.

Before continuing with the description of further embodiments, the determination of a selected dosage and of an injection by the electronics of the PCB 55 is explained with regard to the diagram of FIG. 16, which shows an example course of the signal of a sensor generated during dialing or selecting a dosage and an injection of the selected dosage with the supplementary device 50. The usage of the supplementary device 50 with an injection device 10 begins with mounting the supplementary device 50 on the injection device button 23, which is provided for dosage selection. The supplementary device 50 may automatically detect a mounting, for example by a micro-switch arranged in the carrier interface 51 and activated upon mounting. This detection may trigger a power supply 55 of the electronics of the PCB 54. Then, the user may confirm an initial unit position in order to set an absolute value, particularly a "0" dosage selection. The supplementary device 50 is thereafter ready to use. The user may now select or dial a desired dosage to be injected by the injection device 10 by turning the dial knob 52 for example clockwise. The clockwise turning causes—as described above—sensor signals corresponding to sensor measurements of for example the movement of the free ends of the springs 53, 53' of the supplementary device 50. The measurements typically comprise peaks, for example voltage peaks of a measurement voltage, which correspond to clicks caused by the dosage selection of the user, as illustrated in the diagram of FIG. 16. By counting these peak measurements, the electronics can determine the selected dosage. When the user then pushes the dial knob 52 down, the springs 53, 53' are moved forward to the release button 13 and are pressed on the release button 13 such that the latter is activated for an injection. At the same time, the freely movable ends of the springs 53, 53' are pressed by the pushing of the dial knob 52 on the sensor elements 59, which may detect this pressure and generate a strong signal larger than the peaks, which may be again detected by the electronics as the begin of an injection. The correct end of the injection position or time can be detected by the resetting force (resetting progress) measurable by the sensor elements 59.

Figure 8:
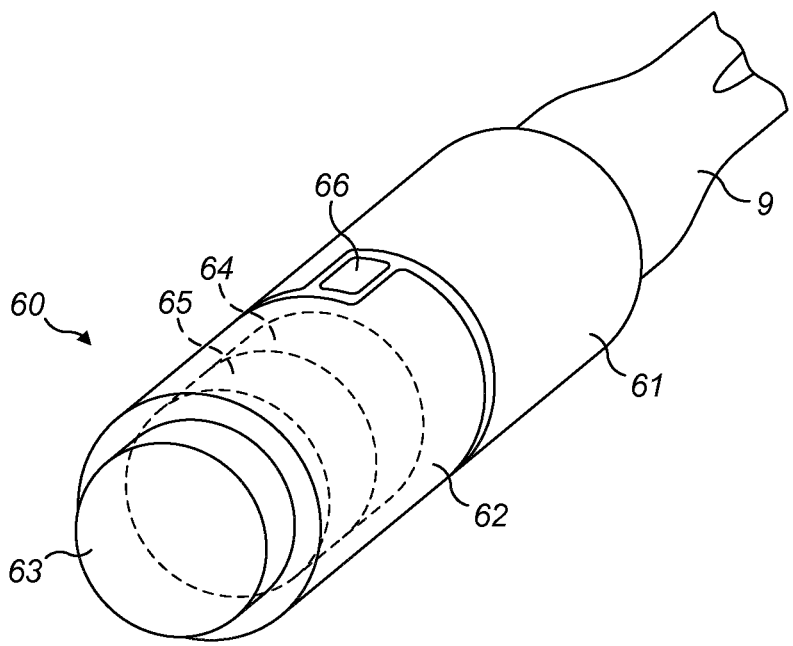
FIG. 8: a perspective illustration of a second embodiment of a supplementary device for releasably attachment to the injection device of FIG. 1 according to an aspect of the present disclosure.

FIG. 8 is a perspective illustration of a second embodiment of a supplementary device 60 to be releasably attached to injection device 10 of FIG. 1. Supplementary device 60 comprises a carrier interface 61 configured to be mechanically coupled to the dosage selector 23 of injection device 10 of FIG. 1, particularly to be clamped on the dosage selector 23 so that a rotation of the interface 61 is transferred to the dosage selector 23. Supplementary device 60 further comprises a dial knob 62 for dosage selection and an injection button 63. Within device 60, a PCB 64 and a battery 65 as power supply for the electronics of the PCB 64 are arranged (dashed lines in FIG. 8). A sensor 66 is made from a quantum tunnelling composite (QTC) material.

Figure 9:
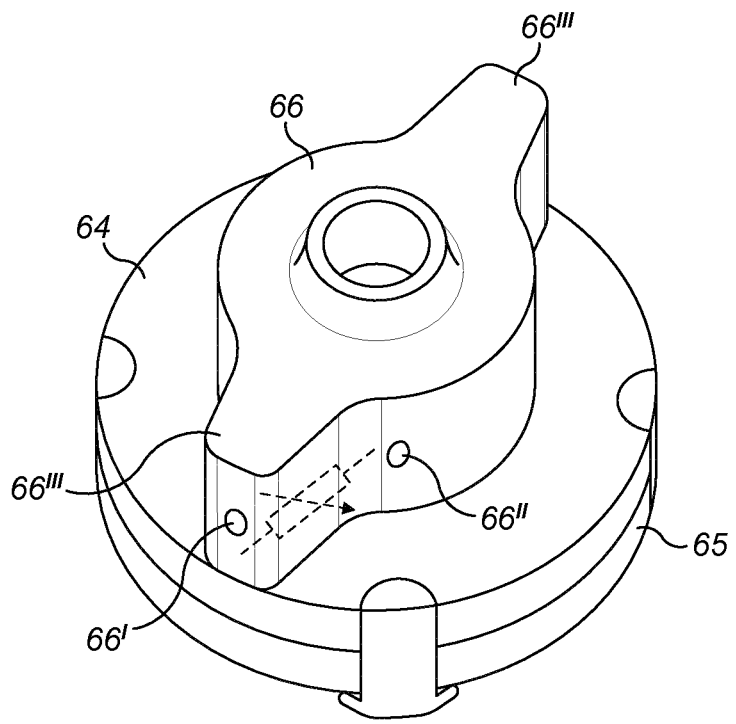
FIG. 9: a perspective illustration of an implementation with a QTC component and its arrangement on a printed circuit board of the second embodiment.
Figure 10:
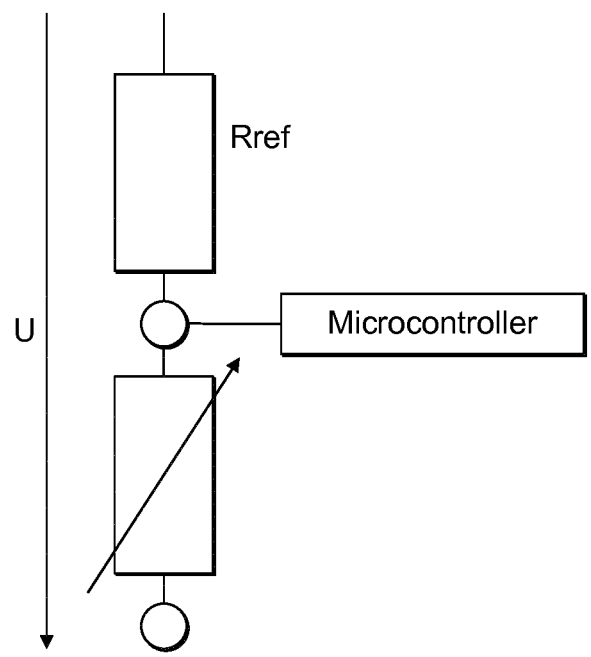
FIG. 10: a circuit diagram of an electronics for determining a dosage selection with the second embodiment of the supplementary device.

FIG. 9 is a perspective illustration of the PCB 64 with QTC component used as sensor 66. The QTC component 66 comprises two blades 66''' arranged opposite to each other. A blade 66'''' may comprise electrical connection points 66', 66" for connection with the electronics of the PCB 64. The surface resistance of the QTC component between the connection points 66', 66" is influenced by pressure exerted on the blade 66'''. The pressure is exerted by the dial knob 62, which is turned by a user for dosage selection. The knob 62 transmits a torque change to the sensor 66, particularly on the blades 66'''. The change of the resistance between the connection points 66', 66" can be detected in order to determine the selected dosage, for example processed by a circuitry as shown in FIG. 10: a microcontroller can be configured to detect the voltage U divided by the voltage divider circuit comprising a reference resistor Rref and the QTC component resistor between points 66', 66".

Figure 11:
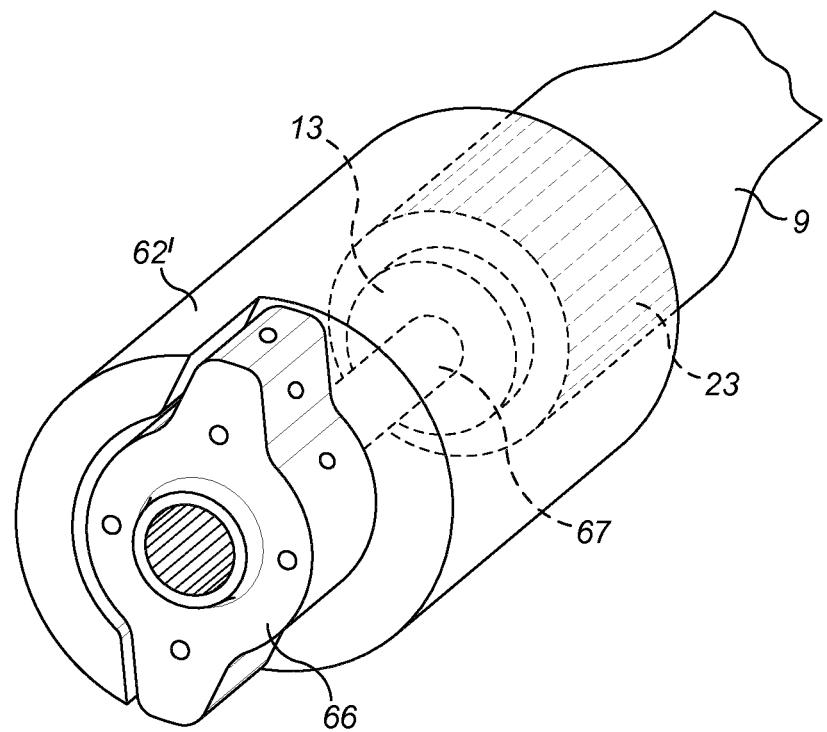
FIG. 11: a perspective illustration of an alternative implementation of the second embodiment.

FIG. 11 is a perspective illustration of an alternative implementation of the second embodiment, wherein the PCB with the electronics can be arranged in an angle of about 90° to the direction of a forcer 67. The dial knob 62', which is illustrated partly transparent in order to show the distal end of the injection device with the release button 13 and the dosage selector 23, is shaped to directly force a pressure in the QTC sensor 66 upon rotation when a user selects or dials a dosage. The forcer 67 transfers a pressure exerted in the axis of the body 9 on the release button 13 to start an injection. The QTC sensor 66 may comprise several surface resistors as represented by the plurality of electrical connection points. All resistors may be for example connected by the electronics of the PCB in parallel so that the lowest surface resistor has a relatively large impact on the total resistance of the parallel connection.

Figure 12:
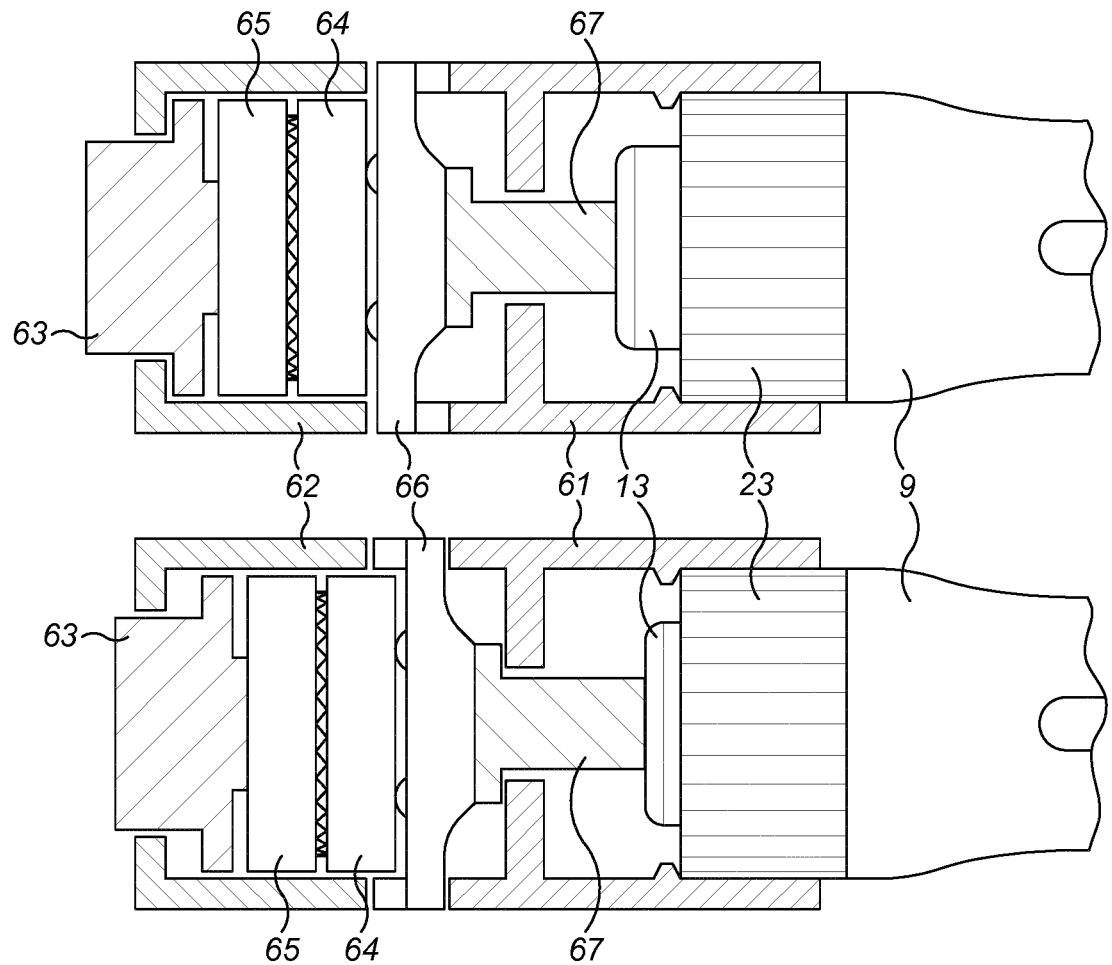
FIG. 12: two cutaway illustrations of the second embodiment with the injection button in two different positions.

FIG. 12 shows two cutaway illustrations of the embodiment from FIG. 8 with the injection button 63 in two different positions. The above illustration shows the status of unused or dialing or selecting a dosage with no pressure exerted on the injection button 63. The below illustration shows the status of an injection, when the injection button 63 is pushed down. In this status, the pressure exerted on the injection button 63 is transferred via the battery 65, the PCB 64, the QTC sensor 66, and the forcer 67 to the release button 13 of the injection device.

Figure 13:
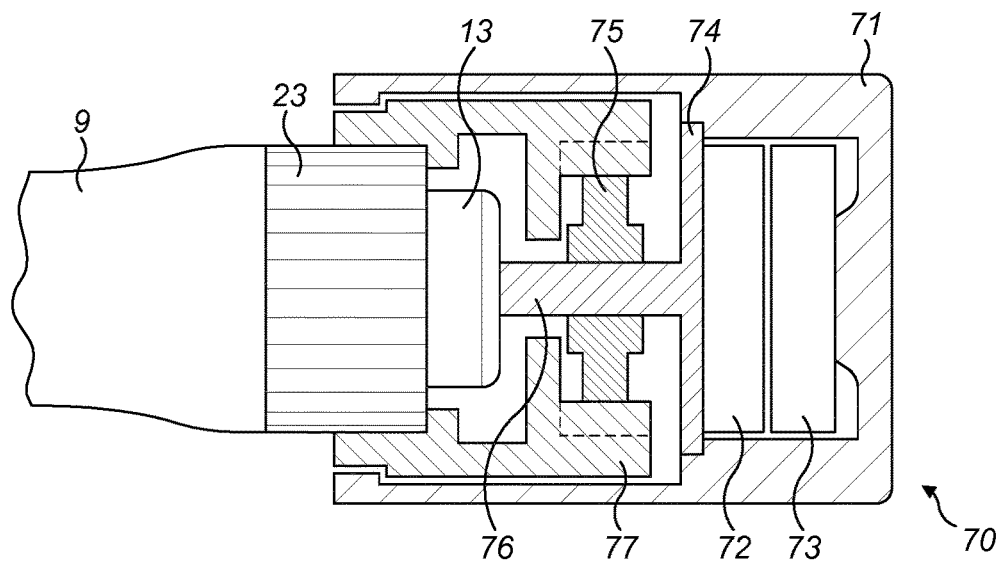
FIG. 13: a cutaway illustration of a third embodiment of a supplementary device for releasably attachment to the injection device of FIG. 1 according to an aspect of the present disclosure.

FIG. 13 is a cutaway illustration of a third embodiment of a supplementary device 70 to be releasably attached to injection device 10 of FIG. 1. Supplementary device 70 comprises a carrier interface 77 configured to be mechanically coupled to the dosage selector 23 of injection device 10 of FIG. 1, particularly to be clamped on the dosage selector 23 so that a rotation of the interface 77 is transferred to the dosage selector 23. Supplementary device 70 further comprises a dial knob 71 for dosage selection. Within device 70, a PCB 72 and a battery 73 as power supply for the electronics of the PCB 72 are arranged. An injection torque pin 74 is provided for transferring a pressure exerted on the dial knob 71 along the axis 76 to the release button 13 for an injection. The injection torque pin 74 extends through a clutch coupling plate being part of the carrier interface 77 and a sensor wheel 75 arranged within the clutch coupling plate.

Figure 14:
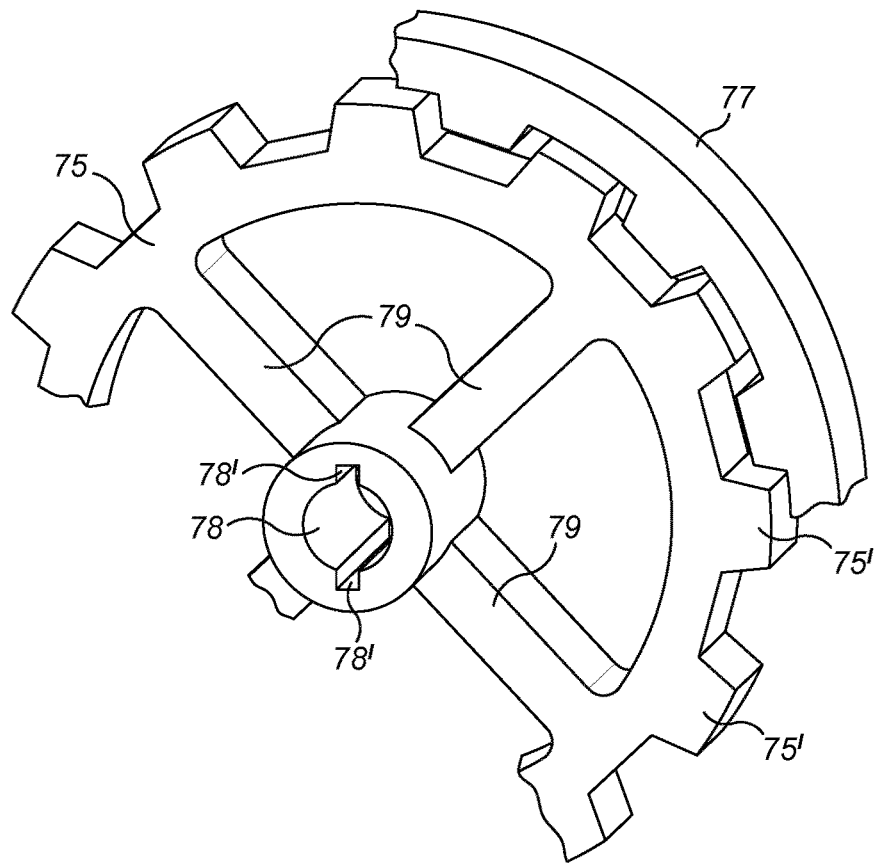
FIG. 14: a perspective illustration of a sensor clutch of the third embodiment.

The sensor wheel 75 and the clutch coupling plate of the carrier interface 77 are shown in detail in FIG. 14. The wheel 75 has at least two spokes 79 and a central bearing 78 through which the injection torque pin 74 may extend. The central bearing 78 comprises anti-rotation locks 78' for preventing a rotation of the pin 74 within the bearing and ensure that a torque exerted on the pin 74 via the dial knob 71 is transferred to the spokes 79 and the wheel 75. The outer contour of the wheel 75 comprises teeth's 75' matching with corresponding teeth's at the inner side of the carrier interface 77. The teeth's may be implemented for a permanent (play free) interface to the dosage selector 23 (more or less teeth's may be necessary).

With at least one of the spokes 79, a sensor element may be implemented. An implemented sensor element detects a bending of the spoke 79. A sensor element may be implemented in various combinations of different sensor techniques and different sensor wheel materials. Combinations may be for example a QTC material combined with a rubber wheel; a force sensing resistor material combined with a plastic wheel; a strain gauge sensor material combined with a plastic or metal wheel.

Figure 15:
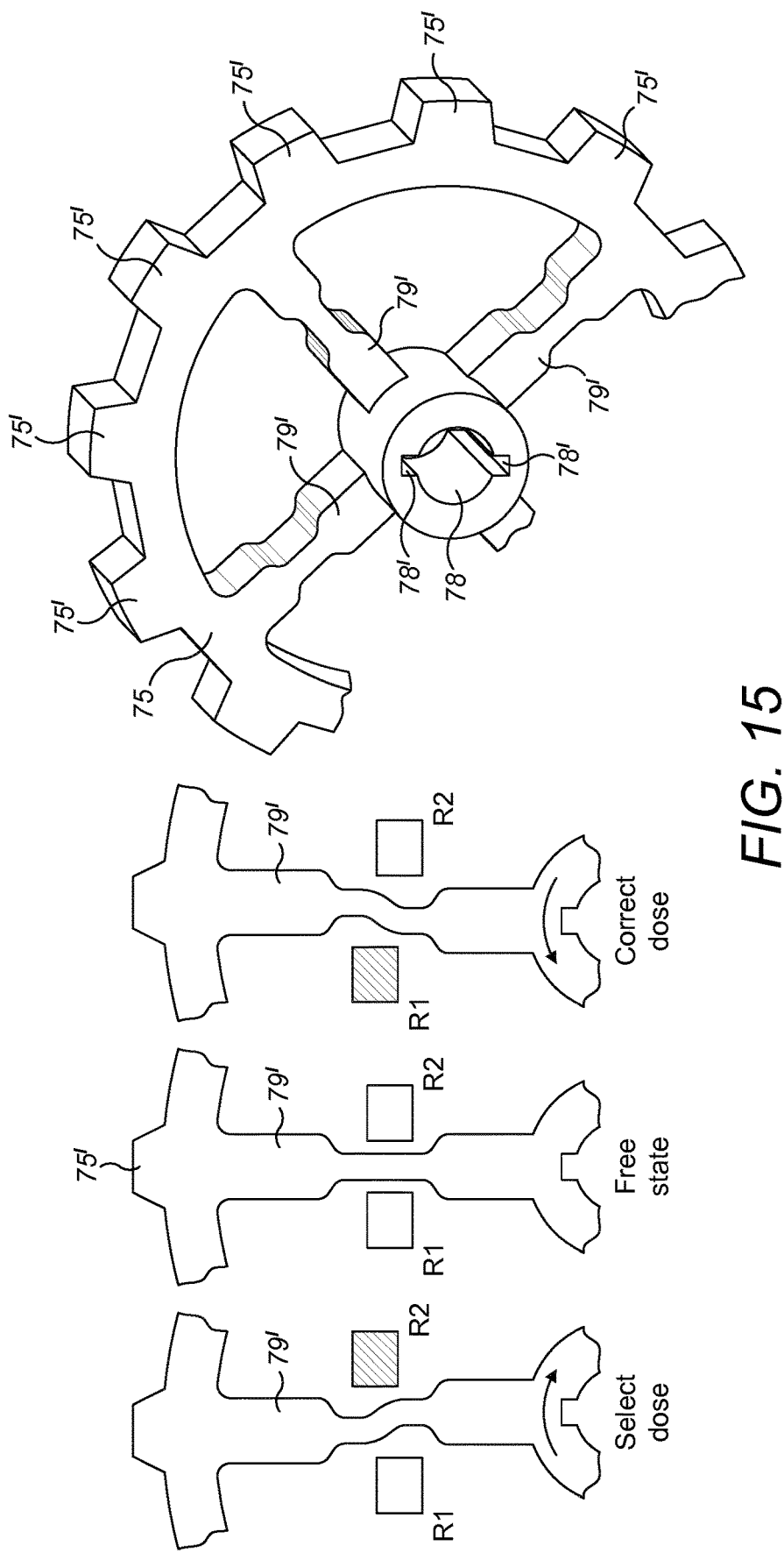
FIG. 15: a schematic illustration of the sensor wheel design of the third embodiment.

Depending on the combination of the sensor technique and the sensor wheel material, the design of the wheel with implement sensor elements may be different. The spokes of the wheel 75 are flexible and are bend upon exertion of a torque on the wheel 75 when a rotation of the wheel 75 is prevented. A wheel 75 with specially designed spokes 79' is shown in FIG. 15. The spokes 79' comprise recesses in which sensor elements R1, R2 are located.

The tapering of the spokes 79' caused by the recesses allows a more extensive bending of the spokes 79' as can be seen in the left illustration in FIG. 15. When a dose is dialled, for example when a user selects a dose by clockwise rotating the dial knob 71 or when the user corrects a selected dose by counter-clockwise rotating the dial knob 71, a torque is transferred from the dial knob 71 via the injection torque pin 74 to the wheel 75, which causes the bending of the spokes 79' as shown in the left and right illustration left in FIG. 15. When no torque is exerted on the wheel 75, it is in a free state and the spokes 79' are not bent, as shown in the middle illustration left. A bending of the spokes 79' activates the sensor elements R1, R2, which can be measured by the electronics of the PCB 72. The resetting force of the wheel 75 (back to the free state) depends on several parameters such as the wheel material, design, particularly of the spokes 79', and the device counterforce.

An injection device may be at least partially retained within the supplementary device as disclosed herein, but may be nevertheless removable from the supplementary device, for instance when injection device is empty and has to be replaced. The injection device and supplementary device may comprise co-operating alignment features to ensure that the supplementary device is correctly orientated and positioned with respect to the injection device. For example, the injection device and supplementary device may be releasably secured together using a bayonet fitting where the injection device has a protrusion on the housing and the supplementary device has a corresponding groove for receiving the protrusion.

Figure 17:
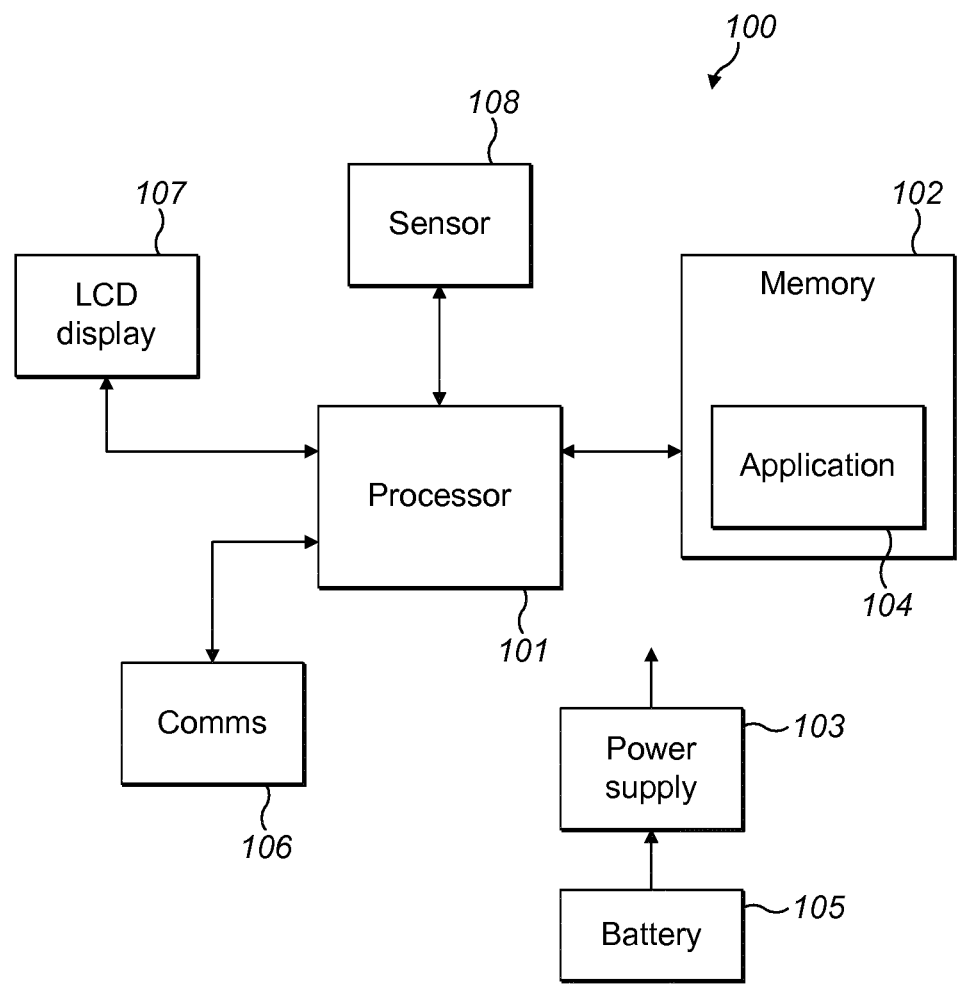
FIG. 17: a block diagram of electronics of a supplementary device.

FIG. 17 is a block diagram of an electronics 100 of the supplementary device. The electronics 100 comprises a processor 101 and a memory 102 storing an operating system for the processor 101 and a software 104 for processing sensor signals and to determine the selected dosage from the processed sensor signals as well as data transmission and receipt. The processor 101 controls a communication circuitry 106, particularly a wireless unit, which is configured to transmit and/or receive information to/from another device in a wireless fashion. Such transmission may for instance be based on radio transmission or optical transmission. In some embodiments, the wireless unit is a Bluetooth transceiver. Alternatively, wireless unit may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, International Units (IU) may be used, or otherwise, the used unit may be transferred explicitly, for instance in coded form. The transmitted data may also include a time stamp associated with an injection.

A battery 105 powers the processor 101 and other components by way of a power supply 103. The attachment of the supplementary device to an injection device can be detected by a sensor or micro-switch being automatically activated, and this can be used as a wake-up or switch on trigger. Thus, the supplementary device may automatically turn on and begin operate when it is attached to an injection device. Similarly, when the supplementary device is detached from an injection device, it may automatically power off, thus saving battery power.

In operation, the processor 101 is configured by the software 104 to receive and process signals output by the one or more sensors 108 of the supplementary device, such as shown in FIG. 16. The processor 101 may count peaks of the sensor signals and derive from the counted peaks a dosage selected by the user. For example, the processor 101 may multiply the number of the counted peaks with a dose unit, which corresponds to one click when the user turns the dial knob of the supplementary device. The processor 101 may be also configured to detect the start and end of an injection from the sensor signals. As mentioned above with reference to FIG. 16, when the injection button is pushed, the output sensor signals may clearly indicate the beginning of an injection, for example by a large peak measurement. If the processor 101 detects such a signal, it may generate a time stamp and store it together with the determined selected dosage in the memory 102. Also, the end of the injection may be detected by the processor 101, and a time stamp may be stored in memory 102. After an injection, the processor 101 may be configured to transmit the stored information related to a selected dosage of a medicament and/or use of an injection device via the communication circuitry 106 to an external electronic device, for example a smartphone or a computer. This information can be also displayed on a display 107 for use by the user of the injection device. The information may be either processed by supplementary device itself, or may at least partially be provided to another device (e.g., a blood glucose monitoring system or a computing device).

The processor 101 may be further configured to record a user's injection history. While the injection device may be a single use auto-injector, the supplementary device is reusable, and is configured to be removed from a used injector and attached to a new injector. The processor 101 of the supplementary device may have an internal clock in order to create time stamps associated with the injection events. The clock may be a relative clock or an absolute clock. The supplementary device may be configured to communicate with an external device through wireless unit 106 and the external device may provide an absolute time.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An example of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g., a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. A supplementary device configured to be attached to a drug delivery device, the supplementary device comprising:
    a carrier interface configured to mechanically couple the supplementary device to a dosage selector of the drug delivery device;
    a dial knob configured to select a dosage to be delivered by the drug delivery device;
    a mechanical coupling configured to transfer a torque from the dial knob to the carrier interface when a dosage selection is made with the dial knob;
    a sensor configured to output signals indicative of the transferred torque; and
    a processor configured to receive the signals output from the sensor and configured to determine the selected dosage based on the received signals.

2. The supplementary device according to claim 1, wherein the mechanical coupling is configured to transfer a compressive force exerted on the dial knob to a release button of the drug delivery device such that the drug delivery device is triggered to cause an injection of the selected dosage.

3. The supplementary device according to claim 2, further comprising a spring configured to force the dial knob into an initial position, in which no compressive force is exerted on the release button of the drug delivery device.

4. The supplementary device according to claim 1, wherein the mechanical coupling comprises at least one spring for transferring the torque,
    wherein a first end of the at least one spring is fixedly coupled to the dial knob and a second end of the at least one spring is configured to exert a force on the sensor upon transferring of the torque via the dial knob,
    wherein the processor is configured to receive signals output from the sensor representing a force measurement of the force and is configured to determine the selected dosage based on the received force measurement.

5. The supplementary device according to claim 1, wherein the mechanical coupling comprises a spring for transferring the torque,
    wherein both ends of the spring are fixedly coupled to the dial knob and the spring is shaped to exert a force on the sensor upon transferring of the torque via the dial knob, and
    wherein the processor is configured to receive signals output from the sensor representing a force measurement of the force and is configured to determine the selected dosage based on the received force measurement.

6. A supplementary device according to claim 1, wherein the mechanical coupling comprises the sensor and the sensor comprises at least one element made of a quantum tunnelling composite material,
    wherein a change of the torque being transferred upon the dosage selection results in a resistance change of the at least one element made of the quantum tunnelling composite material, and
    wherein the processor is configured to receive signals output from the sensor representing the resistance change and is configured to determine the selected dosage based on the received resistance change.

7. The supplementary device according to claim 1, wherein the mechanical coupling comprises a sensor wheel and a pin fixedly coupled to the dial knob and extending through a bearing in the sensor wheel to a release button of the drug delivery device such that exertion of a pressure force on the dial knob is transferred by the pin to the release button.

8. The supplementary device according to claim 7, further comprising a coupling plate,
    wherein the bearing comprises an anti-rotation lock such that a rotation of the pin is transferred to the sensor wheel and the sensor wheel is coupled to the coupling plate such that a rotation of the dial knob is transferred to the sensor wheel, and
    wherein the sensor wheel is coupled to the coupling plate such that a rotation of the sensor wheel is restricted.

9. The supplementary device according to claim 8, wherein the sensor wheel comprises at least two bendable spokes with at least one of the at least two bendable spokes comprising one or more sensor elements of the sensor, wherein the one or more sensor elements are configured to measure a bending of the respective at least one of the at least two bendable spokes, and
    wherein the processor is configured to receive signals output from the one or more sensor elements representing the measured bending and is configured to determine the selected dosage based on the received bending measurements.

10. The supplementary device according to claim 9, wherein (i) the one or more sensor elements are made from a force sensing resistor material and the sensor wheel is made from a plastic material, or (ii) the one or more sensor elements are made from a strain gauge sensor material and the sensor wheel is made from a plastic or metal material.

11. The supplementary device according to claim 9, wherein the one or more sensor elements are made from a quantum tunnelling composite material and the sensor wheel is made from a rubber material.

12. The supplementary device according claim 1, wherein the processor is configured to process the received signals output from the sensor by detecting peak measurements of the output signals indicative of an operation of the dial knob and by counting the measured peaks for determining the selected dosage.

13. The supplementary device according to claim 1, wherein the dial knob comprises a printed circuit board with the processor and a battery for supplying power to the processor of the printed circuit board and the sensor.

14. The supplementary device according to claim 13, further comprising communication circuitry configured to communicate with an external electronic device.

15. The supplementary device according to claim 14, further configured to transmit the determined selected dosage and/or to receive data via the communication circuitry.

16. The supplementary device according to claim 1, further configured to detect when the supplementary device is mechanically coupled to the dosage selector of the drug delivery device and configured to supply the processor with electrical energy upon the detection.

17. The supplementary device according to claim 1, further comprising a display unit and wherein the processor is configured to control the display unit such that the selected dosage is displayed on the display unit.

18. The supplementary device according to claim 1, further comprising at least one memory, wherein the processor is configured to cause information relating to the selected dosage or a last performed injection operation to be stored in the memory upon determining that an injection was made with the drug delivery device, wherein the information comprises at least a time stamp associated with the last performed injection operation.

19. The supplementary device according to claim 1, further comprising at least one memory, and wherein the processor is configured to cause information relating to the selected dosage and a last performed injection operation to be stored in the memory upon determining that an injection was made with the drug delivery device, wherein the information comprises at least a time stamp associated with the last performed injection operation.

20. The supplementary device according to claim 1, wherein the carrier interface is configured to rotationally couple the dial knob of the supplementary device to the dosage selector of the drug delivery device.

21. The supplementary device according to claim 20, wherein the carrier interface is configured to attach to the dosage selector of the drug delivery device to attach the supplementary device to the drug delivery device.

22. A system comprising:
  a drug delivery device; and
  a supplementary device configured to be attached to the drug delivery device, the supplementary device comprising
    a carrier interface configured to mechanically couple the supplementary device to a dosage selector of the drug delivery device;
    a dial knob configured to select a dosage to be delivered by the drug delivery device;
    a mechanical coupling configured to transfer a torque from the dial knob to the carrier interface when a dosage selection is made with the dial knob;
    a sensor configured to output signals indicative of the transferred torque; and
    a processor configured to receive the signals output from the sensor and configured to determine the selected dosage based on the signals.

* * * * *